United States Patent [19]

Rafelson

[11] Patent Number: 4,724,844

[45] Date of Patent: Feb. 16, 1988

[54] VITAL SIGN MODULAR UNIT

[76] Inventor: Stephen Rafelson, 20 Stratford La., Mount Laurel, N.J. 08054

[21] Appl. No.: 748,908

[22] Filed: Jun. 26, 1985

[51] Int. Cl.⁴ .............................................. A61B 5/02
[52] U.S. Cl. .................................... 128/670; 128/696; 312/111; 340/815.12; 5/440
[58] Field of Search ........................... 211/26, 89, 94; 128/670, 695, 696; 340/815.12, 815.2; 297/191; 429/97, 98, 123; 339/152; 312/209, 223, 245; 5/434, 436, 440

[56] References Cited

U.S. PATENT DOCUMENTS

| | | | |
|---|---|---|---|
| 3,229,368 | 1/1966 | Tocchini | 312/209 |
| 3,851,936 | 12/1974 | Muller | 312/245 |
| 3,865,101 | 2/1975 | Saper et al. | 128/419 D |
| 4,085,253 | 4/1978 | Johnson | 429/98 |
| 4,097,113 | 6/1978 | McKelvy | 128/419 D |

Primary Examiner—Joseph Falk
Attorney, Agent, or Firm—Mason, Fenwick and Lawrence

[57] ABSTRACT

A portable vital sign modular unit including a vital sign display case and a modular case. The vital sign modular unit is slidably mounted on a mounting plate. The mounting plate provides an electrical connection to the vital sign display case for powering the display of the vital signs of the patient. The modular case provides a storage area for accessible retrieval of commonly used instruments, such as a blood pressure cuff, required for the measuring of vital signs of the patient. The vital sign modular unit is transferrable between a series of locations having mounting plates.

20 Claims, 18 Drawing Figures

VITAL SIGN MODULAR UNIT

BACKGROUND OF THE INVENTION

Monitoring the vital signs of a patient is important for the management of patients who are in need of frequent routine care. This care may include transporting patients from one location to another within the hospital. The monitoring of vital signs is also important to doctors who practice family medicine, as well as to surgical and nonsurgical specialists, in such fields as otolaryngology, cardiology, and gastroenterology, to name a few.

More and more medical and surgical treatments are being carried out on an outpatient basis and, in many instances, doctors are performing these procedures on patients who, because of their medical history, stand a chance of developing hypertension or hypotension, apnea, bradycardia or tachycardia during the course of the treatment.

Presently available automatic blood pressure, pulse and respiration rate monitors are usually cumbersome, immobile, and very expensive. These monitors are usually permanently located on shelves or in wall units in the ICU of the hospital. The alternatives to these monitors, such as pulse measurement by palpation and blood pressure measurement by aneroid or mercury-filled sphygmomanometers with a manually inflated cuff, are inconvenient. Other monitors, such as portable digital blood pressure and digital pulse measuring devices which are available as home electronic items, are not sufficiently durable to be used in a physician's office or in a hospital.

Rapid and continuous vital sign retrieval is often necessary outside the ICU/CCU setting, especially in those areas where patients receive outpatient surgical and semi-surgical procedures. This applies particularly to those patients at high risk of cardiovascular complications due to preexisting disease and ongoing drug therapy. Present practice outside the ICU/CCU setting involves the use of a blood pressure cuff and mercury filled sphygmomanometer or aneroid sphygmomanometer with auscultation through a stethoscope for Korotkoff sounds, manual timing of pulse rate and manual inflation of a blood pressure cuff.

The areas in medicine where the need exists for compact, inexpensive and versatile vital sign measuring and display units include GI endoscopic surgery, cardiology stress testing, pulmonary medicine, ER/ICU/CCU, intermediate care unit settings for the "not too ill", ENT, dentistry, and oral surgery. In these areas, vital sign measurements such as blood pressure, pulse, temperature and respiratory rate (apnea) are continuously required. Continuous vital sign monitoring particularly applies to patients with significant cardiovascular disease where rapid and accurate assessment of the vital signs of a patient is required.

GI medicine often entails invasive high risk situations such as the evaluation of massive gastrointestinal bleeders, with serious underlying chronic illness such as arteriosclerotic heart disease or chronic obstructive pulmonary disease. Patients are also put at risk while undergoing modern endoscopic therapeutic procedures with esophageal scleroinjection of varices, colonoscopic polypectomy, laser control of bleeding peptic ulcers, sphincterotomy, and balloon dilatation of the lower esophageal, pyloric or oddisphincter. Often a nurse assistant, alone with a patient, has to provide the appropriate dose of drugs, provide the correct accessories, and be certain of the hemodynamics of patients who quite often are old, infirm and sensitive to both sedatives and narcotic analgesics. These situations provide a setting where the treating physician or nurse would require a continuous monitoring of the vital signs of a patient.

SUMMARY OF THE INVENTION

The present invention includes a vital sign display case mounted on top of a modular case forming a vital sign modular unit. The vital sign modular unit provides a physician with a digital display of the vital signs of a patient through which the physician can quickly recognize hypoventilation or apnea, hypotension, or vagal reactions. The vital sign modular unit of the present invention is lighter in weight and smaller in size compared to permanently installed or less mobile vital sign display devices which are presently in use.

The present invention also includes a head support platform. The head support platform includes a device for engaging a portable vital sign modular unit which is located at one end of the head support platform. At the other end of the head support platform is a pillow. In addition, oral suction catheters and accessories for endoscopic procedures may be anchored to the head support platform.

The present invention allows physicians of all specialties, as well as nurses and dentists, to monitor the vital signs of a patient conveniently and quickly and to transfer this capability from one location to another. The compact vital sign modular unit of the present invention is movable from a mounting plate located on a stretcher to a wall mounting plate or to a mounting plate secured behind the head rest of an examining chair. The vital sign modular unit is attachable to a mounting plate secured to an IV pole and to a mounting plate suspended from a ceiling. The adaptability of the present invention to several locations within a room and to different rooms saves time for a treating physician and expense for a hospital. Also, patients in the emergency room or in a postoperative setting, requiring transportation around a hospital or to another location outside the hospital, benefit tremendously from the features of the present invention.

The modular case of the present invention includes a track or tongue and groove design for attaching the modular case to a mounting plate having a complementary shaped track or tongue and groove design. The modular case includes a central storage area for such vital sign measuring equipment as a blood pressure cuff, inflation bulb, respiratory measuring equipment, temperature measuring equipment and pulse measuring equipment which includes a minute and second timer. Vital sign measuring equipment as used with the present invention is manufactured by such manufacturers as Kendall, Timex, Ritter-Tycos, Narco Scientific, IVAC and Physio-Control. An apnea monitor, a device now in use in pediatric units and in many homes for infants at risk from sudden infant death syndrome, may also be stored in the modular case. Apnea monitors are manufactured by Healthdyne and are also available under the trade name Respitrace ®.

The compact size of the vital sign modular unit allows use of the present invention on a stretcher or on top of a bed. The vital sign information displayed by the vital sign display unit is ideally elevated above the head of a patient who is lying on his side next to the vital sign modular unit. The sides of the vital sign modular unit, in some cases, are padded to protect the head of a patient in case of accidental contact with the unit.

The present invention is useful in monitoring adults receiving drugs which may depress their respiratory drive. Another benefit of the present invention is to those patients who require constant monitoring, such as patients being transported or transferred outside the range of permanently anchored vital sign measuring units.

The vital sign display unit of the present invention provides digital display of measured blood pressure, pulse, temperature and respiratory rate (or any combination thereof) of a patient. An alarm may sound upon deviation from preset upper and lower parameter limits for each of these measured vital signs.

The vital sign modular unit is attachable to a mounting plate in any one of a number of different positions. This is made possible by male/female interconnections, such as an interfitting track design or a tongue and groove design, located between the vital sign modular unit and the mounting plate. One part of the male/female interfitting connection between the vital sign modular unit and a mounting plate is located at either the base of the modular case, a face of the modular case or a face of the vital sign display case.

Attachment of the vital sign modular unit to a ceiling is accomplished by securing the vital sign display unit or modular case to a mounting plate which is attached to support struts descending from the ceiling. The mounting plate and the vital sign modular unit include either tracks shaped complimentary to each other or a track and groove shaped complimentary to each other for interconnecting the mounting plate and the vital sign modular unit. The support struts are attachable to tracks mounted on the ceiling, allowing movement of the vital sign modular unit along the path of the tracks.

The length of each side, the top and the bottom of the modular case is approximately 10 to 24 inches and the width is approximately 6 to 12 inches. A height of 8 to 12 inches for the sides of the vital sign display case allows the digital display of the vital sign display case to project above the ear-to-ear dimension of the average patient's head. The sides of the modular case may be padded for posterior head protection and for head support during those applications (gastroenterology-endoscopy of the upper GI tract, etc.) where head support is desirable. The vital sign display case is mounted on top of the modular case for easy visibility of the vital sign data to nearby medical personnel.

A blood pressure cuff is stored within a storage area defined within the modular case. Access to the storage area is obtained through the top or sides of a modular case with a vertically oriented vital sign display case or through apertures defined by the vertical side walls of the modular case with a horizontally oriented vital sign display case. Access is also available from the top of a horizontally oriented vital sign display having a centrally located storage area. Each side aperture of the modular case is partially blocked by nylon-type mesh netting. The sides of the modular case are made of metal or durable plastic framing with the exterior surfaces in some instances being covered with vinyl covered foam which protect a patient in case of accidental contact with the modular case.

The vital sign modular unit is in an alternate embodiment detachably secured to an endoscopy/patient transport head support platform. A recess defined by the base of the head support platform approximates an average pillow's length and width, with a thickness in the range of 3 to 5 inches. A foam pillow fits in the recess defined by the base of the head support platform.

The head support platform of the present invention, used for endoscopic procedures, includes a pillow for elevating the head of the patient approximately 2 to 6 inches from the surface of a bed. The pillow may be elevated to a maximum angle of 30° from the horizontal position by an adjustable support located beneath the pillow. The pillow extends from the front edge of the platform, midway to the rear of the head support platform. The rear of the platform includes a mounting plate for the vital sign modular unit.

Positioning handles and anchoring devices for endoscopic and other accessories may be attached to the periphery of the frame of the head support platform. The anchoring devices are for the holding of biopsy forceps, snares, catheters and syringes. Beneath the mounting plate or support platform there is a space for a rechargeable (nickel-cadmium) or non-rechargeable battery pack to power the display of the vital signs of the patient on the vital sign display case. The battery pack is, in some embodiments, located within the mounting plate. The pillow of the head support platform includes velcro patches, stitched to its bottom, which securely anchor the pillow to velcro receptors located on the moveable portion of the head support platform.

The batteries are charged, by electrical connection to an AC source. A power plug receptacle for receiving a plug electrically connected to a power source is located on the side of the head support platform. The batteries may also be located in the base of the modular case or in the vital sign display case.

The mounting plate includes a contact plate or plug which is aligned respectively with a contact plate or plug receptacle of the modular case when the vital sign modular unit and the mounting plate are mounted together. The alignment of the contact plates (plug/plug receptacle) allows transfer of energy from a power source to charge the batteries and to power the operation of the vital sign display case.

It is an object of the present invention to display measured values of the vital signs of a patient.

It is another object of the present invention to provide a vital sign modular unit having a storage area for storing instruments used to monitor the vital signs of a patient.

It is yet another object of the present invention to provide a vital sign modular unit which is slid on a mounting plate.

It is still another object of the present invention to provide a vital sign modular unit which is slid onto a mounting plate, with the mounting plate located at various locations where the vital sign monitoring of a patient is desired.

It is still yet another object of the present invention to provide a mounting plate for supporting a vital sign modular unit on an intravenous pole, on the back of an examination chair, suspended from a ceiling, on a head support platform or on a wall in either a horizontal or vertical orientation.

DETAILED DESCRIPTION OF THE DRAWINGS

Figure 1:
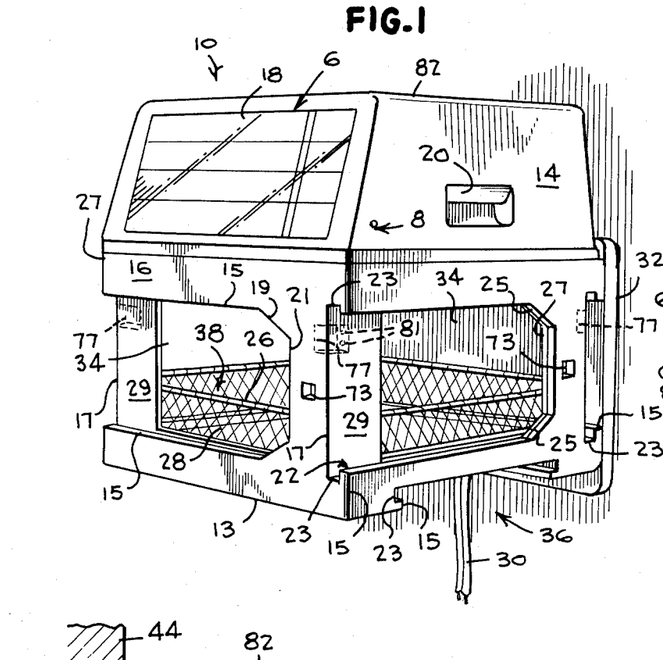
FIG. 1 illustrates a perspective view of a vital sign modular unit mounted on a mounting plate which is secured to a wall.

In FIG. 1, vital sign modular unit 10 includes vital sign display case 14 and modular case 16. The vital sign modular unit, including the vital sign display case and the modular case, defines a housing having a plurality of exterior faces located in different planes. The vital sign display case 14 includes conventional vital sign display circuitry 6 having a digital display face 18, digitally displaying values for blood pressure, heartbeat, respiration and temperature. On one side of the vital sign display case 14 is an indented handle 20, an opposing handle, shown in FIG. 2, being located on the opposite side of the display case. The display case 14 is mounted on the modular case 16 by an interfitting tongue and groove arrangement (not shown), screws (not shown) or permanently affixed to each other.

The modular case includes apertures 34 defined in each of its four side walls. A recess 36 is defined in the bottom 13 of the modular case 16. Apertures 34 and recess 36 include two parallel sides 15 extending from a corner 17 of the modular case. The end of each side 15, opposite to the end extending from the corner 17, terminate in an angled section 19. Angled sections 19 may also be curved. The angled sections 19 terminate in another side 21 aligned perpendicular to the two parallel sides 15. The two parallel sides 15, the two angled sections 19 and the side 21 form the outer surface of groove 22. The inner surface of groove 22 includes parallel sides 23, angled sections 25 and side 27. The exposed exterior surfaces of the side walls of the modular case are padded in some embodiments, to prevent injury to the patient upon accidental contact with the modular case.

The two parallel sides 15 of the apertures 34 extend from the corners 17 of the modular case past exposed corner pillar sections 29. Apertures 34 are spanned longitudinally from corner pillars 29 to side 27 by rigid or deformable cross members 26. Cross members 26 extend parallel to sides 15 of the apertures. Suspended from cross members 26 are nets 28. Storage compartment 38 is formed between the top of the bottom 13 and the four walls of netting 28. Access to storage compartment 38 is obtained through the unblocked portions of apertures 34.

In FIG. 1, the vital sign modular unit 10 is mounted on a mounting plate 12. Rear plate 32, of mounting plate 12, includes a projecting portion 50 (shown in FIGS. 2 and 3) which is shaped complimentarily to the groove 22. In FIG. 1, the mounting plate 12 is shown supporting the rear side surface of the modular case 16. This interconnection is better shown in FIG. 2.

Figure 2:
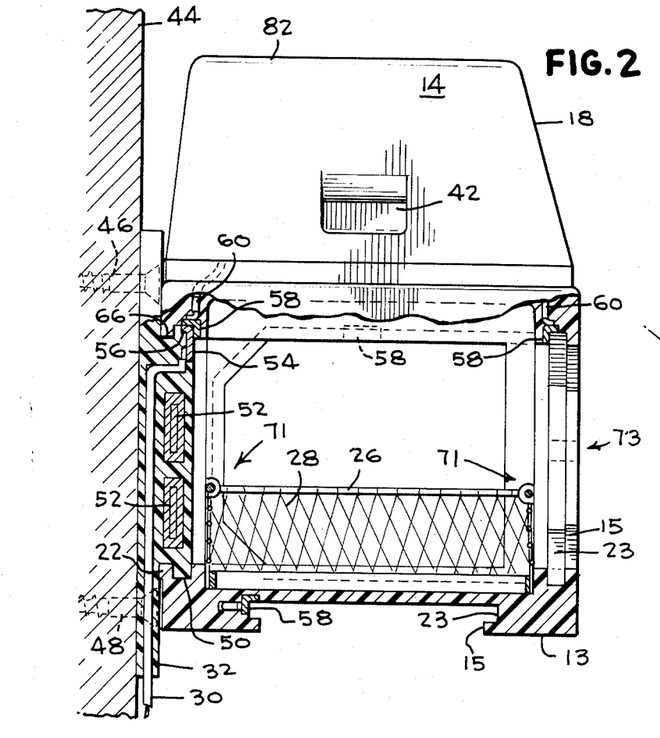
FIG. 2 illustrates a side view of the vital sign modular unit shown in FIG. 1, shown partially in section.

In FIG. 2, indented handle 42 is located opposite to handle 20, shown in FIG. 1. The vital sign modular unit is shown mounted on wall 44. Projecting portion 50 of mounting plate 12 is shown interfitted with groove 22. Electrically conductive cord 30 is connected to contact plate 54 of projecting portion 50. Cord 30 originates from a power source (not shown). Projecting portion 50 of mounting plate 12 may include rechargeable batteries 52. The batteries power the display of measured values for the vital signs of a patient on the vital sign display face 18. Screws 46 and 48 secure the rear plate 32 to the wall 44.

In the embodiment shown in FIGS. 1 and 2, the modular display case is slid from left to right (horizontally) with respect to the stationary mounting plate, when the groove 22 is aligned with the complimentarily shaped portions 56, 66 of mounting plate 12, to interconnect the vital sign modular unit with the mounting plate. Portions 56 and 66 are shaped complimentarily to the groove 22 formed from sides 15, 21, 23, 27 and angled portions 21 and 27. Stop 71 extends from rear plate 32 and is spring-biased. Stop 71 snaps into an opening 73 defined by the modular case 16 or vital sign display case 14 to lock the vital sign modular unit to the mounting plate. To separate the stop 71 from the recess 73, a control lever 81 is operable to depress the stop 71 prior to the sliding of the vital sign modular unit from the mounting plate. The opening 73 extends through the modular case 16 or vital sign display case 14. The stop 71 is depressed by moving lever 81 to retract the stop into the mounting plate and thereby allowing the sliding of the modular case or vital sign display case from the mounting plate.

The vital sign display case 14 may also includes a recess 80 (shown in FIG. 4) for the mounting of the vital sign modular unit on a mounting plate located above the vital sign modular unit. It is to be appreciated that additional recesses may be formed on the left side, right side and rear side of the vital sign display case for receiving a mounting bracket. When additional recesses are located on the vital sign display case, access to the interior of the modular case is available through all four side entrances.

Electrical contact plate 54, located in the middle of the top edge of the extended portion 56 of the projecting plate 50, is electrically connected to batteries 52. Contact plate 54 is aligned to engage, a correspondingly located contact plate 58, located on the top edge of side 15 of the groove 22 formed in each of the side apertures 34 and recess 36 of the modular case 16. Electrical conducting wire 60 is electrically connected at one end to contact plate 58 and at the other end to the vital sign display case 14 for powering the display of the vital signs of a patient. A contact plate 58 is located in each of the side apertures 34 and bottom recess 36 and is electrically connected by wire to the vital sign display case as is shown for the front and rear apertures in FIG. 2.

Figure 3:
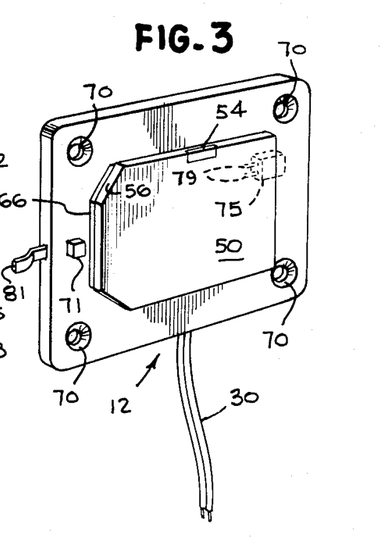
FIG. 3 illustrates a perspective view of a mounting plate.

Electrical contact is, in an alternate embodiment, achieved between plug 75, shown in phantom in FIG. 3, and plug receptacle 77, shown in phantom in FIG. 1. The same electrical connections provided for contact plates 54 and 58 are provided for plug 75 and plug receptacle 77 so that when prongs 79 of plug 75 are forced into openings 81 of plug receptacle 77, electrical contact is made.

Projecting portion 50 of mounting plate 12 is usually fixed to a flat surface by screws extending through screw holes 70 shown in FIG. 3. The grooves 22 of apertures 34 or recess 36 slide across the projecting portion 50 of the mounting plate to hold the mounting plate and vital sign modular unit 10 together. Upon sliding groove 22 of the vital sign modular unit into the complimentarily shaped projecting portion of the mounting plate, to mate the narrow length sides of U shaped portion 56 and 66 with the sides 21 and 27 of the groove 22, the contact plate 54 of the projecting portion 50 aligns with and contacts the contact plate 58. The display face 18 is oriented in a particular direction based on the alignment of one of the apertures 34 or the recess 36 with the mounting plate 12, as shown in FIGS. 1, 2, 4, 5, 6 and 7. The groove or tongue and groove interlocking between the vital sign modular unit and the mounting plate may be horizontally aligned, as shown, or vertically aligned in an alternate embodiment, for up and down, rather than side to side, sliding of the vital sign modular unit on the mounting plate.

Figures 9, 17:
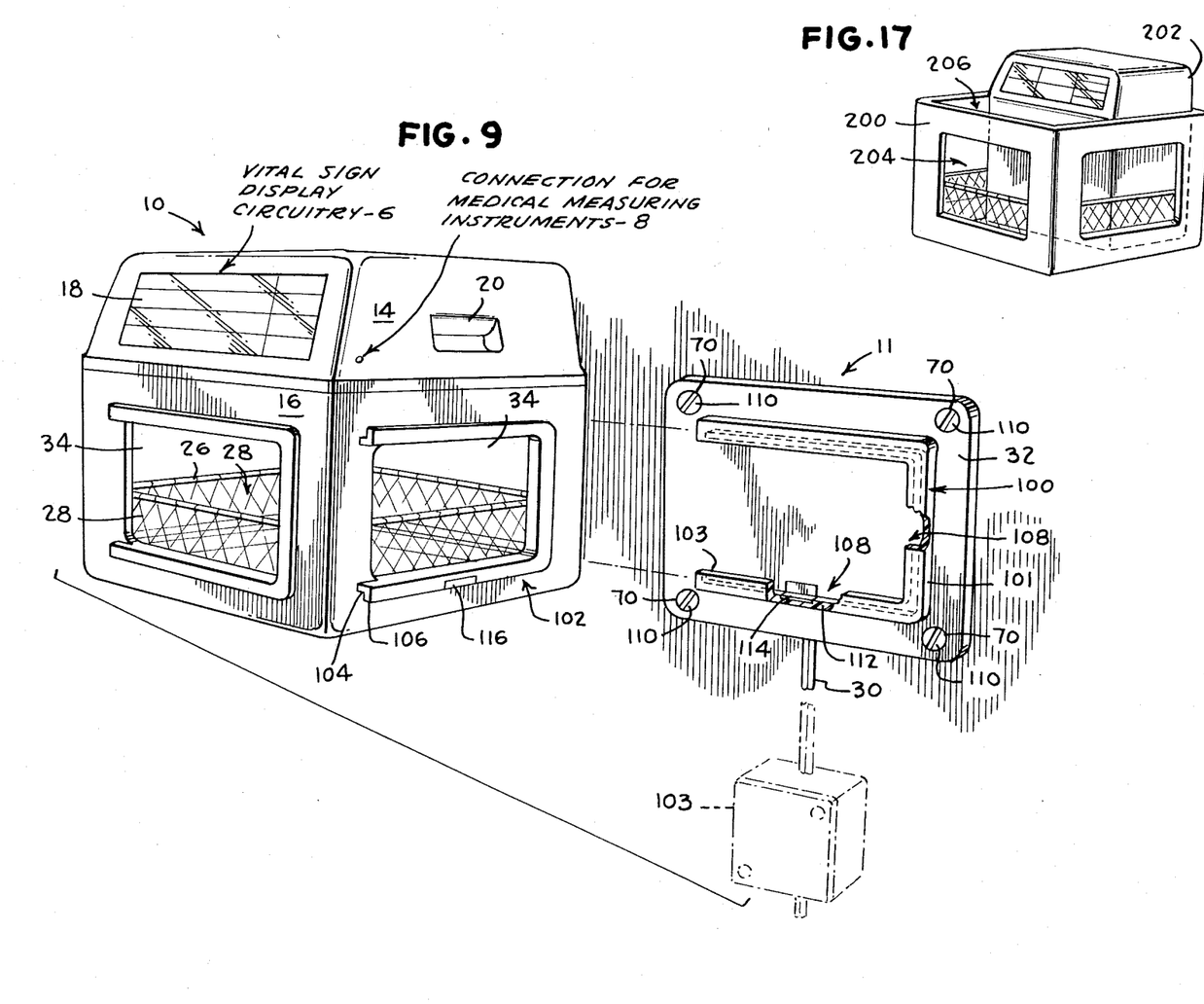
FIG. 9 illustrates a perspective view of a different means, from FIG. 1, for interfitting the vital sign modular unit and mounting plate of the present invention.
FIG. 17 illustrates a vital sign display case mounted vertically in a modular case.

In FIGS. 1, 2 and 9, cross members 26 are shown secured to the inside of the side walls by a screw and washer at 71. The fours sides of netting 28 provide an enclosed storage area 38 for the storage of blood pressure cuffs and other instuments used for measuring the parameters displayed by the vital sign display 18. The instruments measuring the vital signs of a patient are electrically connected (not shown) to the vital sign display case by appropriate connection 8.

In FIG. 9, vital sign modular unit 10 is shown spaced from mounting plate 12. The mounting bracket 11 includes a grooved track 100. U-shaped tongue extension 102 is formed extending from three sides of the apertures 34. The tongue extension 102 includes projecting portion 104 and outwardly extending portion 106. The grooved track 100, as shown in partial cut away section, includes groove 108 defined between the rear plate 32, the interior surface of projecting portion 101 and the interior surface of inwardly extending portion 103. Groove 108 is shaped complementary to tongue extension 102. The tongue extension 102 is slid into grooved section 100 for holding the vital sign modular unit. The rear plate 32 is secured to a surface by screws 110 extending through screw holes 70.

Power cord 30 is attached to electrical contact 112. Electrical contact 112 is connected to electrical contact plate 114. Electrical contact plate 114 contacts electrical contact plate 116, located on the external surface of the tongue extension 102, when the tongue extension 102 is slid into grooved section 100. A tongue extension (not shown) also extends from the top of the vital sign display case 14 and from the bottom of the modular case 16 for interfitting with the mounting plate 11 shown in FIG. 9. In an alternate embodiment for electrical contact, the plug/plug receptacle connection shown in phantom in FIG. 3 may also be applied in FIG. 9.

Rechargeable battery pack 103 (shown in phantom) may be connected in the line of power cord 30. The rechargeable batteries maintain power to the mounting bracket during a power outage. Also, if the mounting bracket is moved or attached to a movable object, such as an IV pole, the battery pack is unplugged from the power source and travels with the mounting bracket. Alternately, rechargeable batteries (not shown) may be incorporated into the base of the modular case or the display case.

Figure 4:
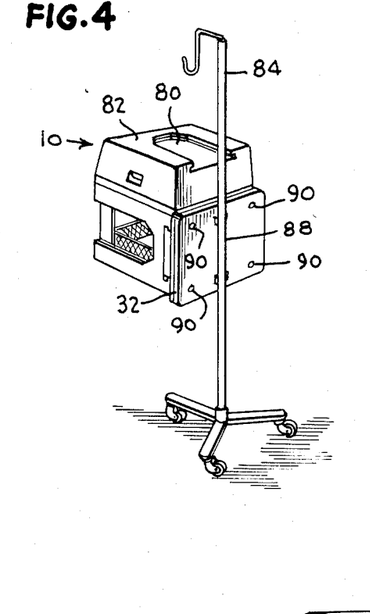
FIG. 4 illustrates a rear perspective view of a vital sign modular unit mounted on a mounting plate which is secured to an IV pole.

In FIG. 4, a vital sign modular unit 10 is shown with a recess 80 defined by the top 82 of the vital sign display case 14. The vital sign modular unit 10 is mounted on an IV pole 84 by the bolting of mounting plate 12 to a plate 86 which is secured to IV pole 84 by anchor clips 88. The bolts 90 secure together mounting plate 12 and plate 86. The vital sign modular unit is slid horizontally onto projecting portion 50 (not shown) of mounting plate 12 to hold the vital sign modular unit 10 in place. In this embodiment, the batteries (as shown in FIG. 2) located in the mounting plate are of a rechargeable type.

Figure 8:
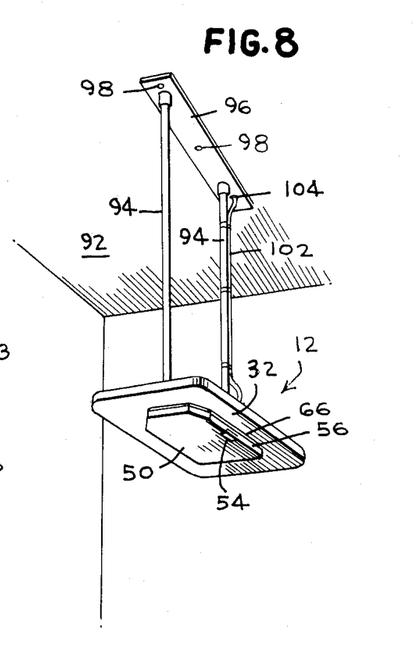
FIG. 8 illustrates a view of a mounting plate suspended from a ceiling by supporting struts.

In FIG. 8, a power source cord 102 extends from an opening 104 in the anchoring plate 96. The power source cord 102 extends to the mounting plate 12 and is electrically connected to the contact plate 54 on the projecting portion 50. The power source cord 102 is connected to a power source (not shown). A plug or plug receptacle (not shown), as shown in phantom in FIGS. 1 and 3, may be included on the projecting portion 50 instead of contact plate 54.

Figure 5:
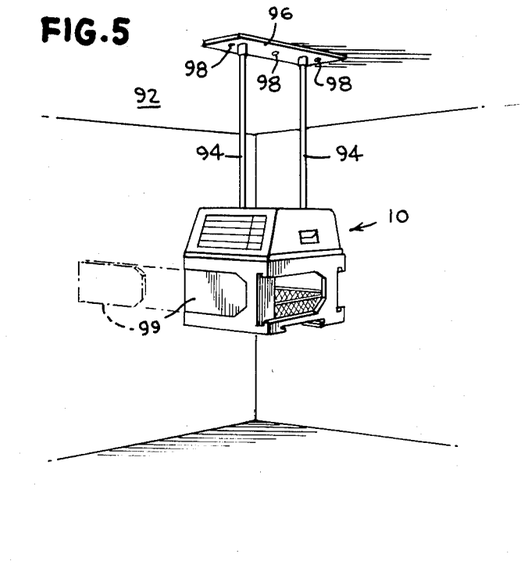
FIG. 5 illustrates a front perspective view of a vital sign modular unit secured to mounting struts which are attached to a ceiling.

In FIG. 5, vital sign modular unit 10 is suspended from ceiling 92 by two parallel struts 94. Struts 94 are anchored at one end to an anchor plate 96. Anchor plate 96 is secured to the ceiling by bolts 98. The other end of the struts 94 are secured to a mounting plate 12 (not shown). The recess 80 of the top 82 of the vital sign display case, as is shown in FIG. 4, is slidably mounted on the projecting portion of the mounting plate to suspend the vital sign modular unit from the ceiling. Alternately, a vertically oriented mounting plate suspended from a ceiling is anchored to the modular case 16 at one of its vertical sides.

In FIG. 5 there is shown a back-up power source. When rechargeable batteries are used in the mounting bracket shown in FIG. 5, there is the possibility that the battery power may be eventually exhausted. Back-up battery pack 99 is shown in FIG. 5, spaced from (in phantom), and inserted in place in, the modular case.

Pack 99 contains rechargeable batteries. An on/off switch (not shown) activates the use of pack 99. Pack 99 is in electrical connection with the vital sign display case when the pack 99, shaped complementary to the side opening of the modular case, is located in a recess defined by the modular case or vital sign display case. The pack 99 includes an electrical contact plate or plug/plug receptacle (not shown) aligned with the electrical contact plate or plug/plug receptacle (not shown) of the side opening of the modular case or vital sign display case for electrical interconnection with the vital sign display.

Figures 6, 7:
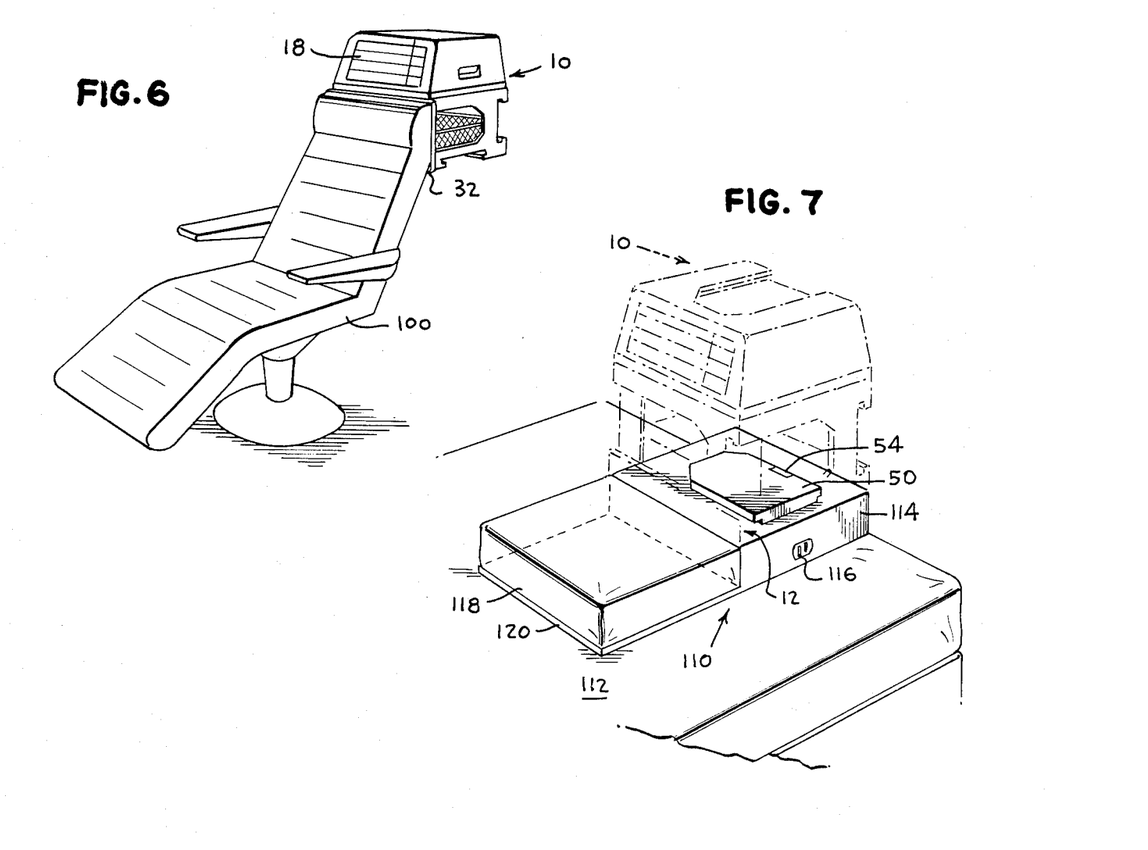
FIG. 6 illustrates a side perspective view of a vital sign modular unit mounted on a mounting plate which is secured to the rear of an examination chair.
FIG. 7 illustrates a side perspective view of a vital sign modular unit, shown in phantom, mounted at one end of a head support platform.

In FIG. 6, rear plate 32 is secured to the back of examination chair 100. The front side aperture, shown in FIG. 1, of the vital sign modular unit 10 is slid over the projecting portion 50 mounted on the rear plate 32 of the mounting plate 12. The digital display face 18 is visible above the head of a patient sitting in the examination chair 100.

In FIG. 17, an alternate embodiment of the present invention is disclosed. A schematic illustration of a modular case 200 is shown. Modular case 200 is understood to include one of the various grooved means for attaching the modular case to a mounting bracket as shown in FIGS. 1 or 9. Vital sign display case 202 is vertically mounted within the modular case 200. The vital sign display case is spaced a distance form the front top edge of modular case to provide access to storage area 204 through top opening 206. It is advantageous for a physician to reach over the top of an examination chair, shown in FIG. 6, and reach down into a modular case storage area 204 through top opening 206 to gain access to a vital sign measuring instruments.

Figures 16, 18:
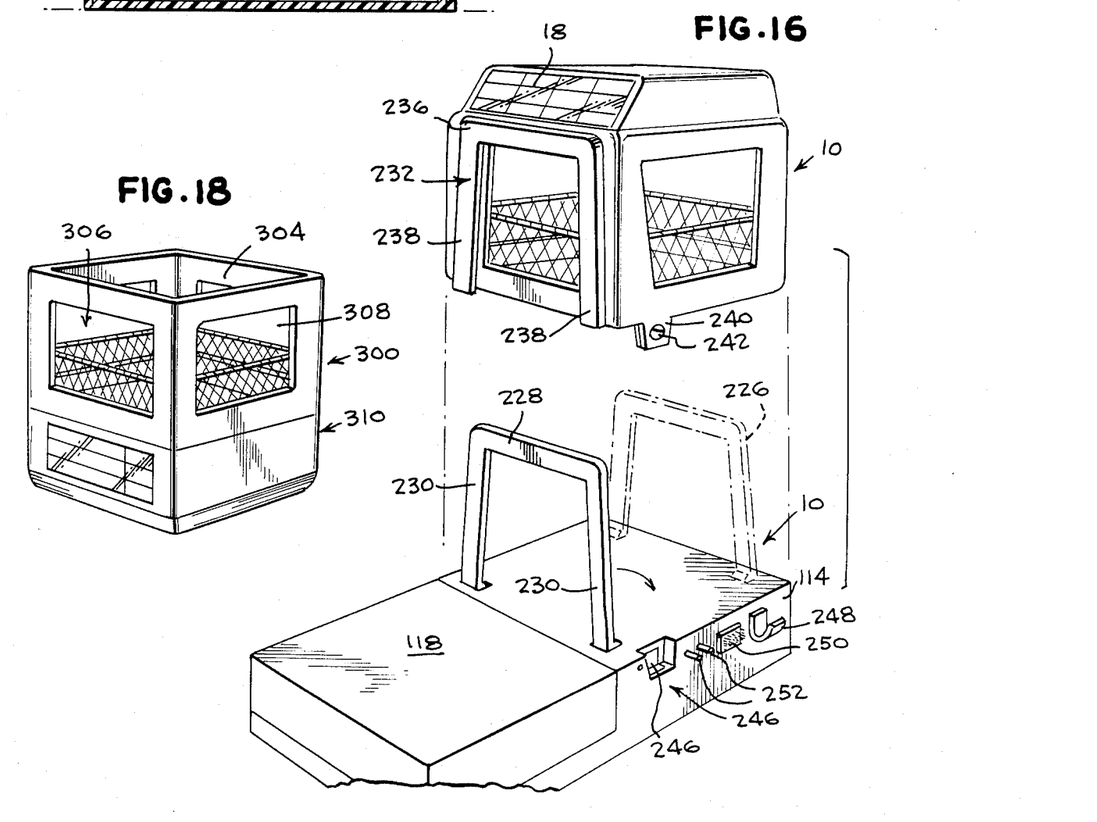
FIG. 16 illustrates a vital sign modular unit with a bar extending from a head support platform.
FIG. 18 illustrates a vital sign display case mounted horizontally on the bottom of a modular case.

In FIG. 18, an alternate embodiment of the present invention is disclosed. A schematic illustration of a modular case 300 is shown. Modular case 300 is understood to include one of the various means for attaching the modular case 300 to a mounting bracket as shown in FIGS. 1 and 9. Also, a mounting means is defined at the underside of vital sign display case 310 for mounting of the vital sign display unit on a mounting bracket. Vital sign display case 310 is horizontally mounted on the bottom of modular case 300. Top 304 of the modular case 300 is completely open. Storage area 306 is accessible through top 304 or side openings 308.

In FIG. 7, a head support platform 110 is shown at one end of a mattress 112. The head support platform includes a base portion 114 having a mounting plate 12 with a contact plate 54 or plug/plug receptacle. A vital sign modular unit 10 is shown, in phantom, engaging the projecting portion 50 of the mounting plate. The base portion 114 of the head support platform includes a power source inlet 116. An electrical plug connected to a power source is inserted into inlet 116 to charge rechargeable batteries (not shown) located within the base portion 114. The batteries are electrically connected to the contact plate 54 or plug/plug receptacle and inlet 116. At the end of the base portion 114 opposite to the mounting plate 12 is a pillow 118. The pillow is secured to a tiltable plate (not shown) by velcro strips. The pillow supporting plate is tiltable to an angle of 30°, pivoting about edge 120 of the base 114. When the pillow is lifted to an angle of 30°, access to the storage area of the vital sign modular unit is obtained through the two side and rear apertures of the modular case. The front aperture is usually blocked by the elevated pillow or the head of the patient resting on the pillow. The vital sign display is visible above the head of the patient located on the pillow even when the pillow is elevated.

Figures 10, 11, 13:
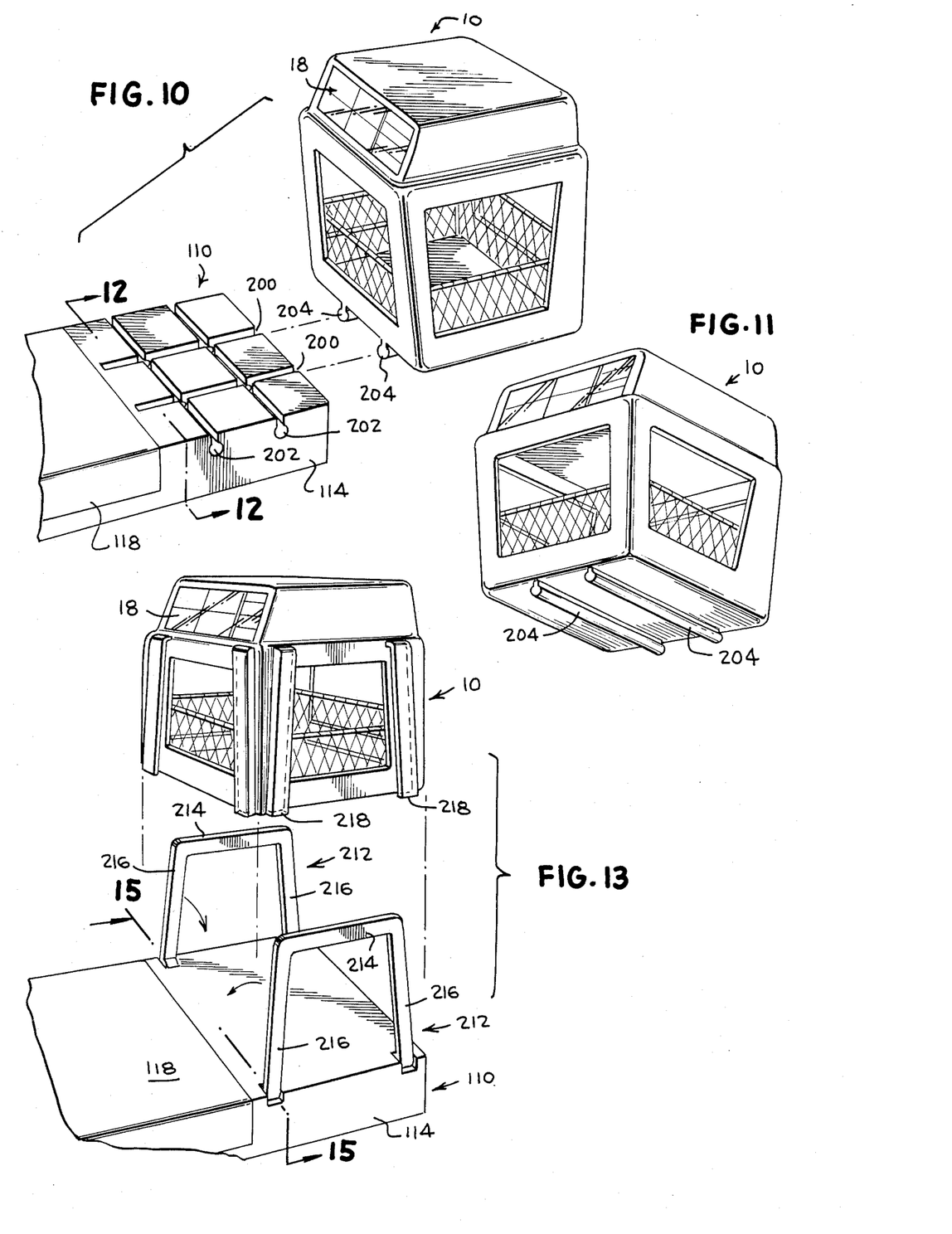
FIG. 10 illustrates a vital sign modular unit having guide rods extending from its bottom surface for insertion into a support platform.
FIG. 11 illustrates a perspective view of a vital sign modular unit having two guide rods extending from its bottom.
FIG. 13 illustrates a vital sign modular unit and an alternate means of holding the vital sign modular unit on a head support platform.
Figure 12:
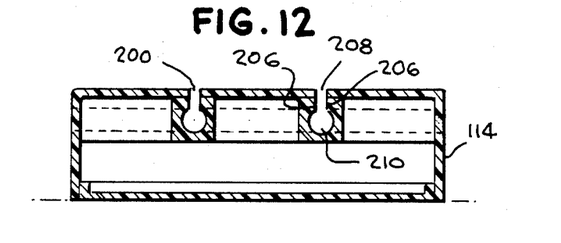
FIG. 12 illustrates a sectional view taken along the line 12—12 shown in FIG. 10.

In FIG. 10, head support platform 110 includes a base 114 defining parallel grooves 200 and parallel grooves 202 which are perpendicular to grooves 200. The bottom of the vital sign modular unit includes one set of projecting rods 204 which are aligned parallel to each other, as is shown in FIG. 11. The rods 204 are shaped complimentarily to the tracts 200 and 202. As shown in FIG. 12, the tracts 200 include parallel side walls 206 forming a channel 208 terminating in cylindrical opening 210. The rods 204 are slidable into the tracts 200 or tracts 202 from either ends of the rods 204. The vital sign modular unit and the direction of display of the vital sign display 18 is thereby aligned in one of four directions on the base 114.

Figure 14:
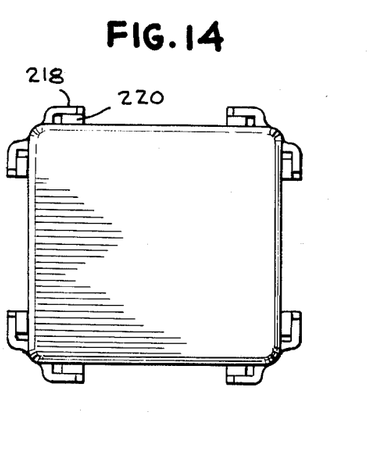
FIG. 14 illustrates a bottom view of the vital sign modular unit shown in FIG. 13.
Figure 15:
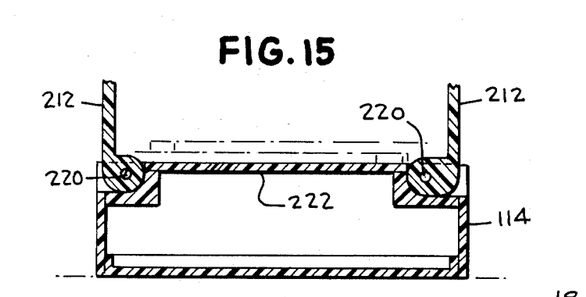
FIG. 15 illustrates a sectional view taken along the line 15—15 shown in FIG. 13.

In FIGS. 13 through 15, a track and groove arrangement is shown for orienting the vital sign modular unit on the head support platform 110 in one of four directions. Projecting from one end of the head support platform 110 are two U-shaped bars 212. The bars in their vertically extending position are aligned parallel to each other. Each bar 212 includes crosspiece 214 and outwardly diverging legs 216. Vital sign modular unit 10 includes projections 218 defining grooves 220 shaped complimentarily to bars 212. Groove 220 and projections 218 are shown in FIG. 14.

The vital sign modular unit is vertically lowered onto the head support platform until the ends of the groove 220 engage the crosspiece 214. The two bars 212 hold the vital sign modular unit in position on the head support platform 110. The vital sign display 18 is oriented in one of four directions depending on the orientation of the vital sign display unit 10 with respect to the bars 212 when the unit 10 is slid down on top of the bars 212.

In FIG. 15, each of the bars 212 are shown pivotably mounted on base 114. Each of the bars rotate about axial pin 220 mounted below the top surface 222 of the base 114. The bars 212 are foldable towards each other to lie one on top of the other. The height of each of the bars is such that the crosspieces 214 fail to extend beyond the periphery of the base 114.

In FIG. 16, folding bar 224 is shown which is similar to bar 212 in FIG. 13. In the embodiment shown in FIG. 16, one folding bar 224 is sufficient to anchor the vital sign modular unit 10 on the head support platform 110. Folding bar 226, shown in phantom, is used if the single bar is located at the rear rather than the middle of the base 114. Folding bar 224 includes crosspiece 228 with outwardly diverging side legs 230. Bar 224 is shaped complimentarily to U-shape extension 232 located on the front side of the modular case. Extension 232 defines U-shape groove 234. Extension 232 includes crosspiece 236 and outwardly diverging side legs 238 for accepting the crosspiece 228 and outwardly diverging legs 230 of bar 224 when the vital sign modular unit, with extension 232, is lowered vertically onto bar 224.

The vital sign modular unit 10 shown in FIG. 16 includes projecting tab or plug 240, preferably having screw 242. Complimentarily shaped receiving recess 244 includes electrical contact plate or plug receptacle 246. When the vital sign modular unit 10 shown in FIG. 16 is vertically lowered onto bar 224, projecting tab or plug 240 fits within recess 244 and provides electrical connection between contact plate or plug receptacle 246 and vital sign display 18. The vital sign display is powered as was previously described for FIG. 7.

Base 114 of head support platform 110, shown in FIG. 16, preferably includes three types of endoscopic, radiologic, cardiac or ENT instrument anchoring devices. Hook 248 extends from the side of the base 114 for holding and endoscopic or other instrument having a protrusion hookable onto hook 248. Velcro patch 250 is attachable to a corresponding velcro patch located on an instrument to be secured to the head support platform. Rubber bars 252 are spaced from one another for holding an endoscopic instrument therebetween. The instrument is of a slightly greater width than the space between the bars 252 and is held therebetween due to the resilient characteristics of the rubber bars. It is advantageous to have endoscopic instruments readily accessible to a treating physician when performing an endoscopic procedure on the patient lying on the head support platform 110. The present invention also provides a constant display of the vital signs of a patient during the endoscopic or other interventional procedure.

The vital sign modular unit of the present invention has been shown secured to a mounting plate located in various locations. The mounting plate may either (1) contain rechargeable batteries, (2) contain rechargeable batteries electrically connected to a power source or (3) be directly connected to an external power source.

The foregoing disclosure and drawings are merely illustrative of the principles of this invention and are not to be interpreted in a limiting sense. It is to be understood that there is no desire to be limited to the exact details and construction shown and described, because obvious modifications will occur to a person skilled in the art.

I claim:

1. A vital sign modular unit for displaying the vital signs of a patient, said vital sign modular unit comprising:
    a housing having a plurality of faces on its exterior, each of said faces being located in a different plane, said housing including an electronic vital sign display unit for displaying the vital signs of a patient;
    a central storage area defined within said housing for storage of medical instruments used to obtain the vital signs for the patient;
    medical instruments adapted to be coupled to the display unit and the patient for displaying vital signs measured by the instruments;
    an aperture defined by at least one of said plurality of faces for gaining access to said central storage area each of said apertures being surrounded by a mounting groove formed on each of said faces of said housing; and
    mounting means interfitting with each of said mounting grooves to support said housing, said mounting means being shaped complimentary to said mounting grooves, each of said mounting grooves having substantially the same shape.

2. The vital sign modular unit as claimed in claim 1, wherein said mounting means includes a projection and said mounting groove is shaped complementary to said projection.

3. The vital sign modular unit as claimed in claim 2, wherein said mounting groove is U-shaped and includes a crosspiece interconnecting two legs, said projection engages the crosspiece and legs of said mounting groove when said mounting means interfits with said mounting groove.

4. The vital sign modular unit as claimed in claim 1, wherein said mounting means includes an extension shaped in an L-shape having two legs with an interior surface and defining a groove between a base of said mounting means from which said extension extends and said interior surface, and said mounting groove is formed by a projection extending from said housing in an L-shape having two legs, one leg of said projection slideably fitting in said groove.

5. The vital sign modular unit as claimed in claim 1, further comprising
    electrical contact means mounted on said mounting groove and being electrically connected to said display means,
    electrical contact means mounted on said mounting means,
    power means electrically connected to the electrical contact means of said mounting means for powering said display means, and
    an electrical connection between said electrical contact means of said mounting groove and said electrical contact means of said mounting means when said mounting means interfits with said mounting groove.

6. A vital sign modular unit as in claim 1, wherein said housing is formed in the shape of a cube.

7. The vital sign modular unit of claim 1, further comprising:
    elongated platform means divided into forward and rearward portions, said forward portion for supporting the head of a patient, and said rearward portion including means for supporting said housing; and
    second mounting means for mounting on said platform means and interfitting with said mounting groove at said bottom of said housing to support said housing, said second mounting means being shaped complimentary to said mounting groove.

8. The vital sign modular unit as claimed in claim 7, wherein a platform defined by said platform means supports said housing and locates said display means above the head of a patient when the patient's head is rested on the platform.

9. The vital sign modular unit as claimed in claim 7, further comprising
    electrical contact means mounted on said mounting groove being electrically connected to said display means,
    electrical contact means mounted on said mounting means,
    power means electrically connected to the electrical contact means of said mounting means for powering said display means, and
    an electrical connection between said electrical contact means of said mounting groove and said electrical contact means of said mounting means when said mounting means interfits with said mounting groove.

10. The vital sign modular unit as claimed in claim 8, wherein said platform includes anchoring means for anchoring medical instruments on the periphery of said platform.

11. The vital sign modular unit as claimed in claim 7, further comprising
    electrical contact means extending from said housing being electrically connected to said display means,
    a recess defined by said platform means, electrical contact means being mounted in said recess, and power means for powering said display means being electrically connected to the electrical contact means mounted in said recess, said electrical contact means mounted in said recess and said electrical contact means extending from said housing being electrically connected when said mounting means interfits with said mounting groove.

12. The vital sign modular unit of claim 1, further comprising:

battery means shaped complimentary to said mounting groove for interfitting within said mounting groove to power said electronic display means when said battery means is supported by one of said mounting grooves on the exterior of said housing.

13. The vital sign modular unit as claimed in claim 12, wherein said battery means includes an electrical contact means and said mounting grooves each include an electrical contact means, said electrical contact means of said battery means being aligned with and electrically connected to said electrical contact means of one of said mounting grooves when said battery means is supported by said one mounting groove.

14. The vital sign modular unit as claimed in claim 13, wherein said battery means includes rechargeable batteries electrically connected to said electrical contact plate means of said battery means.

15. The vital sign modular unit as claimed in claim 13, wherein said display means is electrically connected to said electrical contact means of said mounting grooves.

16. The vital sign modular unit of claim 1:

wherein each mounting groove and mounting means including one of a plug and a plug receptacle shaped complimentary to said plug for electrically interconnecting said mounting groove and said mounting means when said mounting means interfits with said mounting groove.

17. A vital sign modular unit as claimed in claim 16, wherein said one of said plug and said plug receptacle included with said mounting groove being electrically connected with said display means.

18. A vital sign modular unit as claimed in claim 17, wherein said one of said plug and said plug receptacle included with said mounting means being electrically connected to a source of power for electrically powering said display means when said mounting means interfits with said mounting groove.

19. A vital sign modular unit as claimed in claim 16, further comprising battery means shaped complimentary to said mounting groove, said battery means being supported by one of said mounting grooves on the exterior of said housing.

20. A vital sign modular unit as in claim 16, wherein said housing is formed in the shape of a cube.

* * * * *